United States Patent [19]
November

[11] 3,958,446
[45] May 25, 1976

[54] DISCONTINUITY SUPPRESSION APPARATUS FOR VIBRATION DENSITOMETERS

[75] Inventor: Milton H. November, Hacienda Heights, Calif.

[73] Assignee: International Telephone and Telegraph Corporation, New York, N.Y.

[22] Filed: Aug. 20, 1975

[21] Appl. No.: 606,026

[52] U.S. Cl. .............................................. 73/32 A
[51] Int. Cl.² ........................................ G01N 9/00
[58] Field of Search .......................... 73/32 R, 32 A

[56] References Cited
UNITED STATES PATENTS

| | | |
|---|---|---|
| 3,706,220 | 12/1972 | Miller .................................. 73/32 |
| 3,713,324 | 1/1973 | Miller et al. ......................... 73/32 |

*Primary Examiner*—Herbert Goldstein
*Attorney, Agent, or Firm*—A. Donald Stolzy

[57] ABSTRACT

An improved well for a densitometer probe for immersion in a pipeline around the probe to effect a flow of a portion of the fluid flowing in the pipeline through the improved well and through and around the probe while increasing the usable range of the instrument.

9 Claims, 21 Drawing Figures

DISCONTINUITY SUPPRESSION APPARATUS FOR VIBRATION DENSITOMETERS

This application has subject matter, a portion of which is common to that of copending application Ser. No. 548,276 filed Feb. 10, 1975, by M. H. November for DENSITOMETER PROBE SHIELD AND WELL.

BACKGROUND OF THE INVENTION

This invention relates to vibration densitometers, and more particularly to a well in which a densitometer probe can be contained in a manner to increase the densitometer accuracy over a wider density and vibrational frequency range.

In the past, the density versus frequency characteristic curves of vibration densitometers have followed a known law over certain ranges, but have had abrupt changes at one or more points. These abrupt changes have made it virtually impossible to calibrate beyond the said point or points. The accuracy and range of prior art vibration densitometers have thus been limited.

SUMMARY OF THE INVENTION

In accordance with the apparatus of the present invention, the above-described and other disadvantages of the prior art are overcome by providing front and rear holes covered with a mesh to permit flow through a well adapted to receive a vibration densitometer probe.

The above-described and other advantages of the present invention will be better understood from the following detailed description when considered in connection with the accompanying drawings.

BRIEF DESCRIPTION OF THE DRAWINGS

In the drawings which are to be regarded as merely illustrative.

DESCRIPTION OF THE PREFERRED EMBODIMENTS

Figure 1:
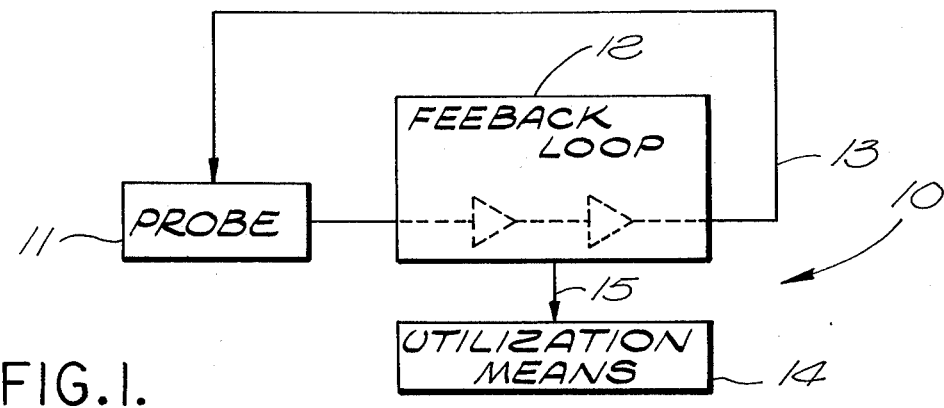
FIG. 1 is a block diagram of a vibration densitometer.

In FIG. 1, a vibration densitometer 10 is shown including a probe 11, a feedback loop 12 connected from and to probe 11 via a lead 13, and utilization means 14 connected from another output 15 of loop 12. Densitometer 10 may be identical, if desired, to that disclosed in U.S. Pat. No. 3,677,067. Attention is also invited to U.S. Pat. No. 3,741,000. By this reference hereto, the entire contents of both of these patents are hereby incorporated in their entireties herein hereat.

Figure 8:
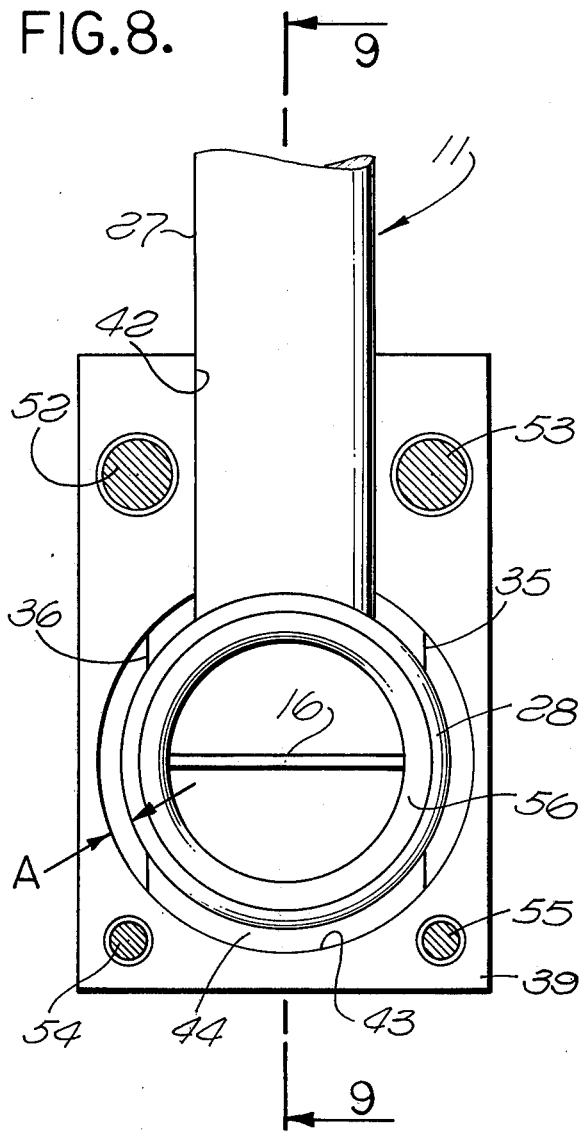
FIG. 8 is a vertical elevational view similar to that shown in FIG. 6 with the vibration densitometer probe inserted in one-half of the probe shield.

Probe 11 contains a vane 16 shown in FIG. 8 which is vibrated. Vane 16 is vibrated because the probe has a piezoelectric crystal pick-up, not shown, the output of which is amplified and the vane 16 vibrated by a magnetostrictive driver, not shown. The resonant vibrational frequency of vane 16 is a known function of the density of the gas or liquid or other fluid in which the vane 16 is immersed.

If desired, loop 12 in FIG. 1 may have a linearization circuit so that the output signal on lead 15 may have a magnitude directly proportional to density.

Utilization means 14 may be a voltmeter or ammeter calibrated in density, a process controller, a gas flow computer, a net oil computer or otherwise.

In accordance with the foregoing, the word "densitometer" is hereby defined to include or not include utilization means 14. Note will be taken that the densitometer in many cases will be manufactured and sold without any utilization means 14. Such utilization means 14 would be supplied by the customer.

The vibration densitometer 10 is essentially an electromechanical oscillator. The oscillator obviously has losses. Loop 12, therefore, includes at least one amplifier. Two amplifiers 17 and 18 are illustrated in loop 12 in FIG. 1.

Figure 2:
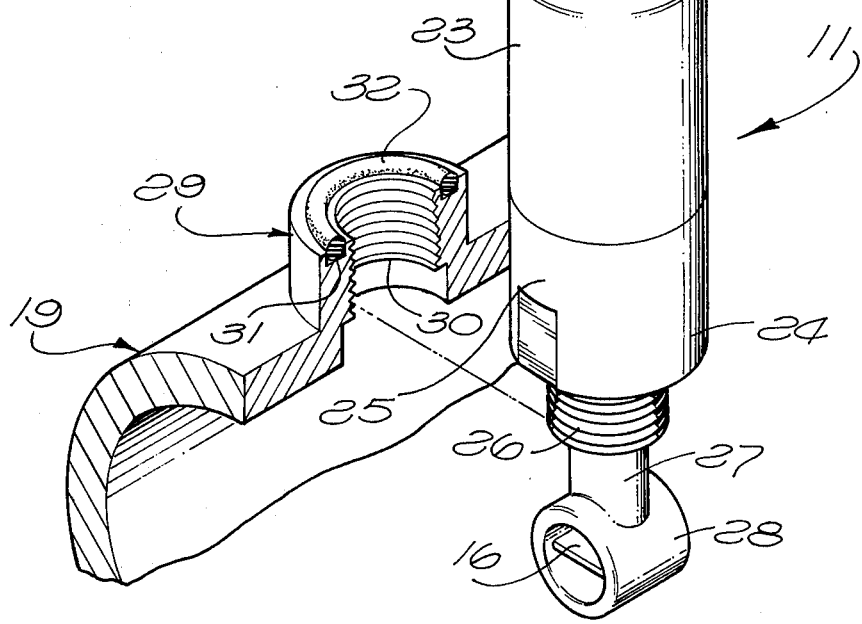
FIG. 2 is an exploded perspective view of a vibration densitometer probe, a portion of its mount and a portion of a pipeline.

Probe 11 is shown again in FIG. 2 for mounting in a pipeline 19.

Densitometer 10 may, alternatively, be, if desired, identical to that disclosed in said U.S. Pat. No. 3,741,000.

The probe 11 may be identical to the probe shown in the said U.S. Pat. No. 3,741,000 with certain exceptions. All these exceptions are noted hereinafter.

The said U.S. Pat. No. 3,741,000 is referred to hereinafter as the "later" patent.

The probe 11 is identical to the probe of the said later patent except for the addition of conduits 20 and 21, and a pull box 22. Conduits 20 and 21 and pull box 22 simply serve as enclosures for the output leads from probe 11 to loop 12 shown in FIG. 1.

Conduit 21 is threaded to pull box 22 in a manner now shown. Conduit 20 is threaded to pull box 22 and to a body 23 of probe 11. Conduits 20 and 21, pull box 22 and body 23 are, thus, all fixed together. A body 24 is fixed to body 23. Body 24 has an upper portion 25 of a larger diameter and a lower portion 26 of a smaller diameter that is externally threaded. A shank 27 is fixed to threaded portion 26 and to a cylinder 28. Vane 16 is mounted in a fixed position along its opposite edges to cylinder 28, as shown in both FIGS. 2 and 8.

Pipeline 19 has a hollow cylindrical projection 29 permitting probe 11 to be lowered thereinto, projection 29 having an axis perpendicular to the axis of pipeline 19. Projection 29 is internally threaded at 30. Probe portin 26 is threaded into projection 29 at the thread 30. Projection 29 has an O-ring groove 31, and an O-ring 32 therein that seals with a shoulder, not visible in FIG. 2, at the bottom of probe portion 25 where the diameter of the probe is reduced to the diameter of the threaded portion 26 thereof. The bottom surface of the probe portion 25 may be flat and in a plane perpendicular to the vertical axis of the probe 11 so as to rest on O-ring 32, O-ring 32 thereby sealing probe 11 inside pipeline 19. At least that portion of probe 11 below the thread 26, thus, protrudes downwardly inside pipeline 19 below the inside diameter thereof.

All the structures shown in FIGS. 1 and 2 may be entirely conventional, if desired.

Figure 3:
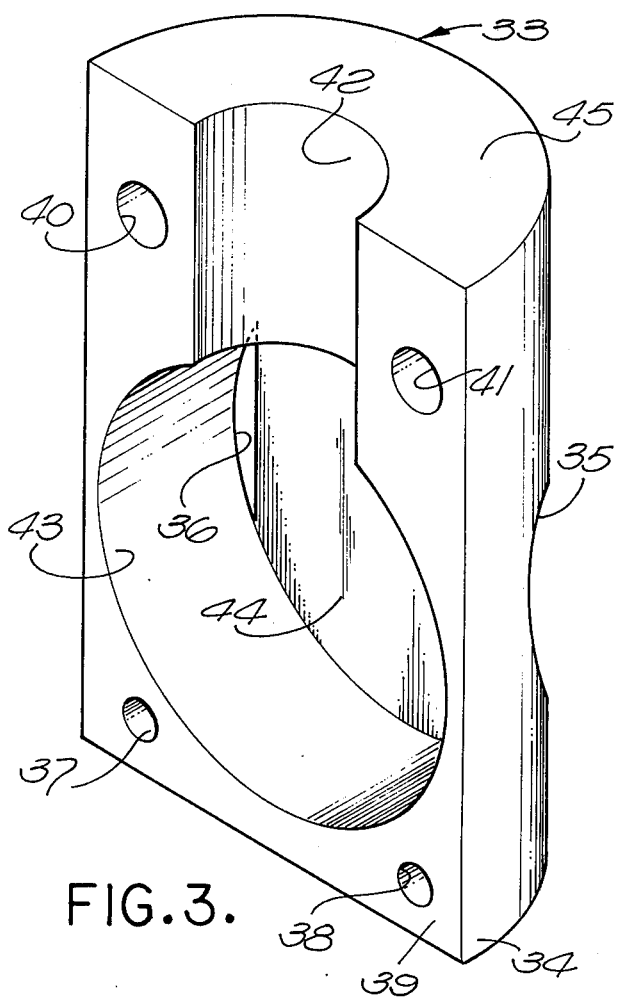
FIG. 3 is a perspective view of one-half of a probe shield, both halves of the probe shield being substantially identical.

In accordance with the present invention, the structures of FIGS. 1 and 2 may be modified by placing a shield around shank 27 and cylinder 28. Both halves of the shield are substantially identical. One-half of the shield is indicated at 33 in FIG. 3. Shield half 33 has a generally cylindrical external surface at 34. However, this cylindrical surface is interrupted by vertical slots 35 and 36. Holes 37 and 38 extend perpendicularly completely through shield half 33. Holes 37 and 38 have axes which are normal to a flat surface 39. Holes at 40 and 41 similarly have axes perpendicular to surface 39 and go completely through shield half 33.

The holes 37 and 38 are somewhat smaller than the holes 40 and 41. However, all of the holes 37, 38, 40 and 41 serve the same general purpose. An Allen head screw is positioned in each of the holes 37, 38, 40 and 41 to hold the two shield halves together. The screws for the holes 37 and 38 cause surface 39 therebetween to abut the corresponding surface in the other shield half.

Shield half 33 has a vertical half bore 42 which may be slightly smaller than the diameter of shank 27 so that the screws of holes 40 and 41 can clamp both shield halves against shank 27 and hold the shield in a fixed position relative thereto.

Shield half 33 has another partial cylindrical bore 43, the axis of which is normal to the axis of the bore 42. Bore 43 terminates in a flat surface 44 which is generally circular except for the slots 35 and 36. Surface 44 is parallel to surface 39.

In manufacture, the openings 35 and 36 are conveniently provided at the same time that bore 43 is provided in that the bore 43 is extended to an extent such that the boring tool interrupts the external surface 34 of shield half 33 and thereby provides the apertures 35 and 36. However, boring is stopped short of going completely through the shield half 33 leaving material, one surface of which is illustrated at 44.

Figure 4:
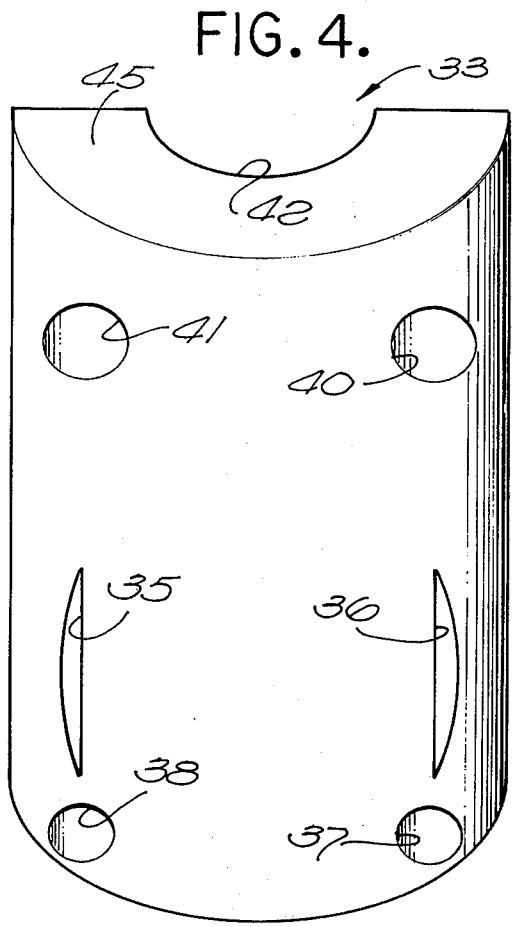
FIG. 4 is another perspective view of the probe shield shown in FIG. 3.

Shield half 33 is again shown in FIG. 4. Note will be taken in both of the FIGS. 3 and 4 that the shield half 33 has an upper flat surface 45 which is generally semicircular and lies in a plane perpendicular to the axis of bore 42.

Figure 5:
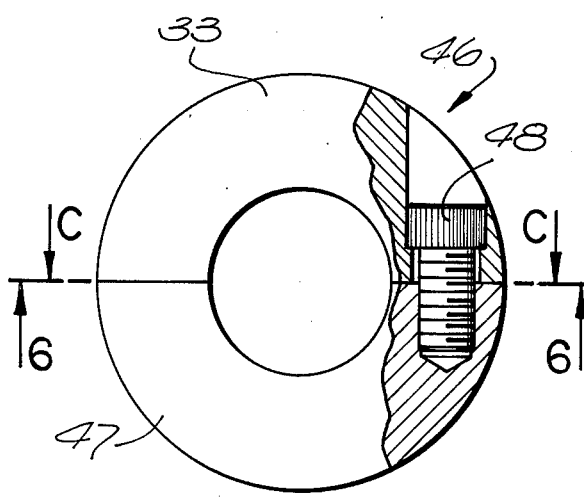
FIG. 5 is a top plan view of the probe shield, partly in section.

The entire shield is illustrated at 46 in FIG. 5. Shield half 33 is shown in FIG. 5 with the other shield half 47. A typical Allen head screw 48 is shown in FIG. 5. All four of the screws may be identical except for their diameters.

Figure 6:
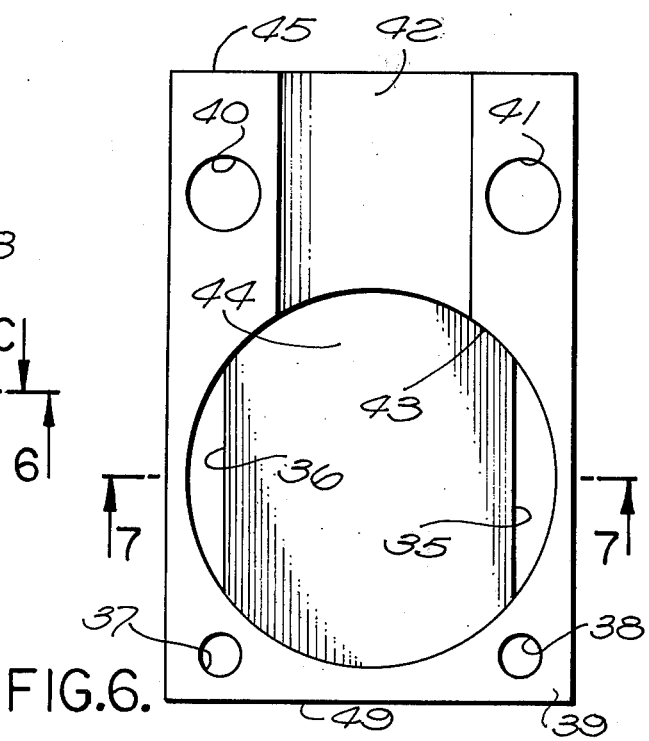
FIG. 6 is an elevational view of a probe shield half taken generally in the direction of the line 6—6 shown in FIG. 5.

Shield half 33 is again shown in FIG. 6. Note that the upper and lower surfaces 45 and 49, respectively, of shield half 33 in FIG. 6 are flat and parallel. Surface 49 has the exact shape of one-half of a circle.

Figure 7:
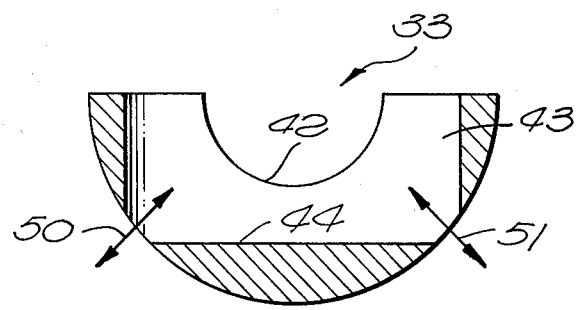
FIG. 7 is a transverse sectional view of the probe shield half taken on the line 7—7 shown in FIG. 6.

Shield half 33 is again shown in FIG. 7 having openings allowing ingress and egress of fluid in the direction of arrows 50 and 51.

In FIG. 8, screws are shown at 52, 53, 54 and 55. The view of FIG. 8 is quite similar to the view of FIG. 6 with shield 46 clamped onto probe shank 27. Shield half 33 is shown in FIG. 8.

In FIG. 8, note will be taken that a cylinder 56 is fixed inside cylinder 28. This construction is described in the said U.S. Pat. No. 3,677,067. cylinders 28 and 56 are substantially the same length and are substantially flush at each of their opposite ends. They are somewhat rounded at each of their opposite ends.

In FIG. 8, note will be taken that cylinder 28 is everywhere a distance A from bore 43. However, shield halves 33 and 47 are clamped tightly upon probe shank 27, as shown in both FIGS. 8 and 9.

In FIG. 9, probe 11 is shown again with shield halves 33 and 47 clamped tightly to probe shank 27. Shield half 47 has one of its two openings indicated at 56.

Figure 9:
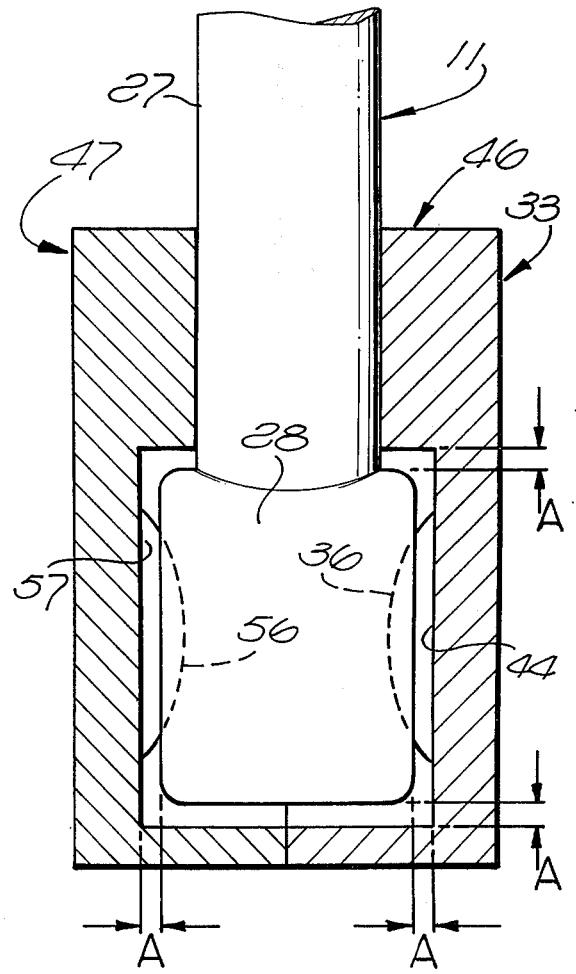
FIG. 9 is a vertical sectional view, partly in elevation, taken on line 9—9 of the structure shown in FIG. 8.

In FIG. 9, it will be noted that except for the three openings 35, 36 and 56, and the fourth symmetrical one, not shown, shield 46 encases an assembly which includes cylinder 28 and vane 16. The same is not fluid tight except for openings 35, etc., but it may be fluid tight, and it allows very little fluid flow into or out of the shield 46 except for the openings 35, etc.

Again, in FIG. 9, note will be taken that cylinder 28 is spaced from surface 44, a corresponding surface 56 of shield half 47, and completely around the external surface of cylinder 28 as shown in both FIGS. 8 and 9, and as shown at A in both FIGS. 8 and 9.

Although probe 11 may or may not be made of heavier materials such as stainless steel, shank 27, cylinder 28 and cylinder 56 may be made of stainless steel. Vane 16 may be made of Ni-Span-C. Shield 46 need not necessarily be made of a lighter material and need not necessarily be made of aluminum, but is preferably made of aluminum.

Figure 10:
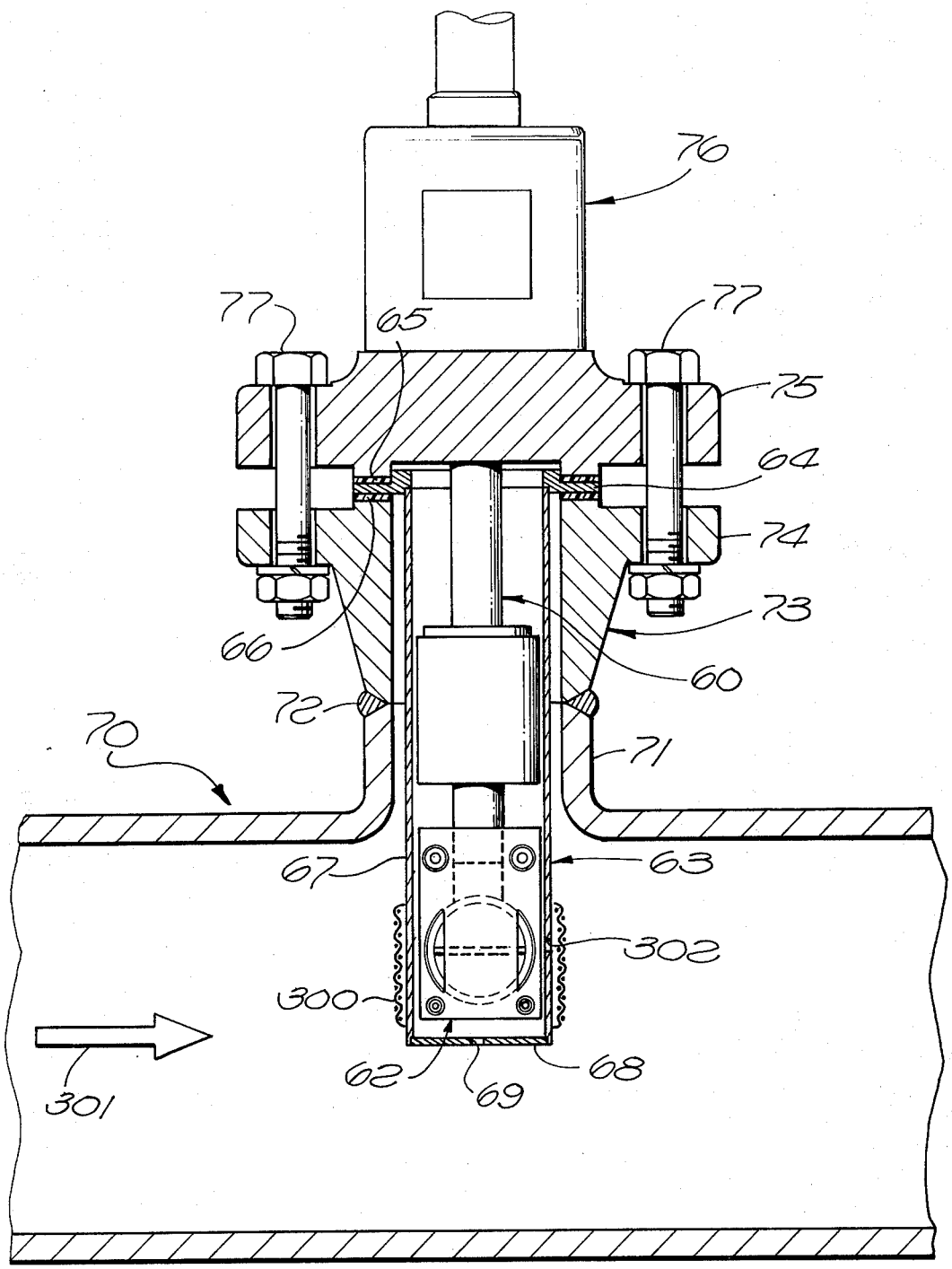
FIG. 10 is a vertical sectional view, partly in elevation, through a pipeline having a shielded densitometer probe mounted in a well therein in accordance with the present invention.

A modification of the invention is illustrated in FIG. 10. FIG. 10 includes a densitometer probe 60 having a vane 61 and a shield 62 located in a well 63. Well 63 is formed of a ring 64 having annular gaskets 65 and 66 bonded on opposite sides thereof. A cylinder 67 then has an upper open end sealed to ring 64 and a disk 68 sealing the lower end thereof except for a drain hole 69. A 50 to 100 micron mesh 300 of a cylindrical shape substantially completely surrounds cylinder 67 and may be brazed thereto at its upper and lower edges.

If fluid flow is in the direction of an arrow 301, a hole 302 forms a fluid exit hole.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

Figure 11:
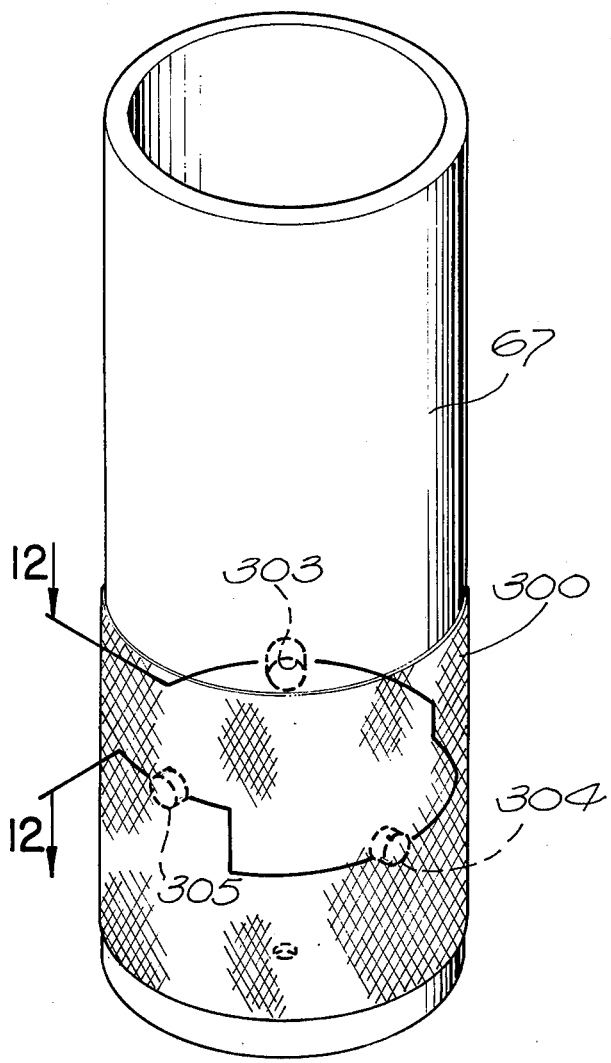
FIG. 11 is a perspective view of the well shown in FIG. 10.

In FIG. 11, cylinder 67 is again shown with mesh 300 bonded thereto.

Figure 12:
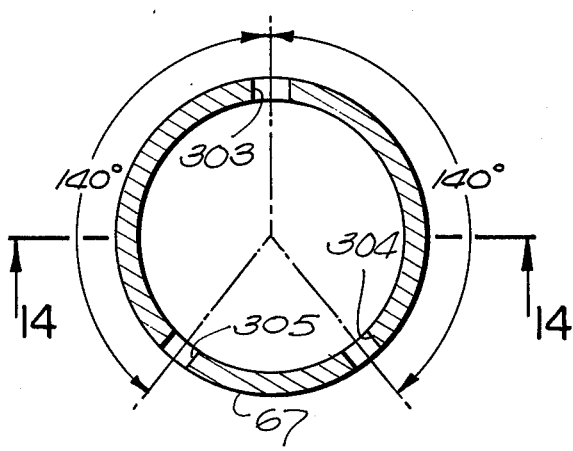
FIG. 12 is a horizontal sectional view through the well taken on the line 12—12 shown in FIG. 11.

In FIG. 12, note will be taken that cylinder 67 has a hole 303 at the location of vane 61, a hole 304 below the location of vane 61, and at an angle of +140° from the axis of hole 303.

Still further, a hole 305 is provided which is above vane 61, and is located −140° from hole 303. The angles in the cases of holes 304 and 305 being clockwise and counterclockwise, respectively.

Figure 13:
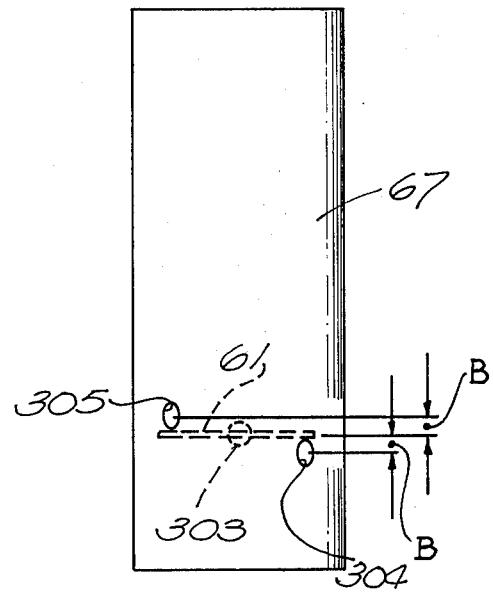
FIG. 13 is an elevational view of the well of the present invention.
Figure 14:
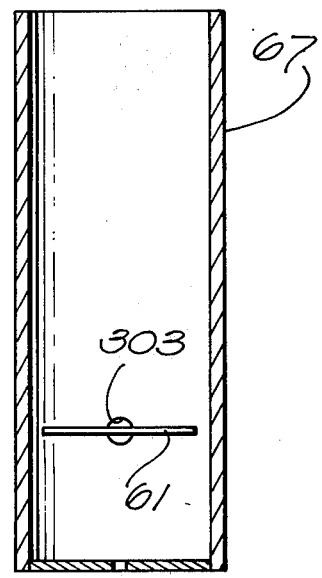
FIG. 14 is a vertical sectional view of the well constructed in accordance with the present invention taken on the line 14—14 shown in FIG. 13.

In FIG. 13, holes 304 and 305 are shown in relation to cylinder 67 and vane 61. Typical dimensions are illustrated at B. The dimension B may be, for example, 3/16 inch. In FIG. 14, the axis of hole 303 may be located at the center of a circle 306, if desired.

Figure 15:
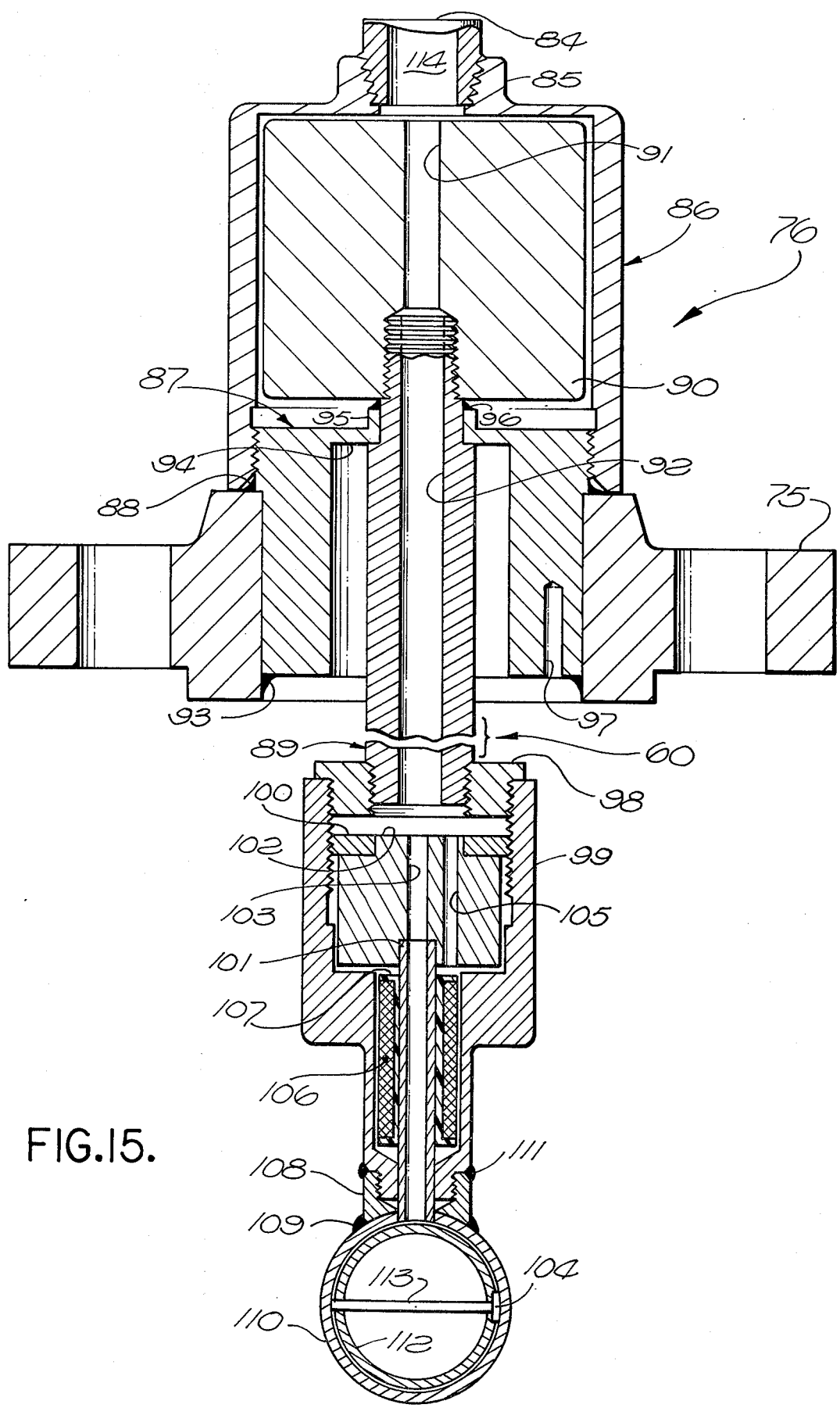
FIG. 15 is a vertical sectional view through the densitometer probe illustrated in FIG. 10.

A vertical sectional view of probe 60 is shown in FIG. 15 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto.

A ring 100 is threaded into body 99. A magnetostrictive tube 101 which is hollow and open at both ends is press fit into a body 102. Body 102 is similar to a body disclosed in the said U.S. Pat. No. 3,741,000, and may be identical thereto, if desired. Alternatively, body 102 may have one hole 103 to receive lead wires from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends, at the bottom thereof, through a circular hole in cylinder 110 and bears against the external cylindrical surface of a cylinder 112. A vane 113 is fixed inside cylinder 110 in a manner identical to that illustrated in the said U.S. Pat. No. 3,677,067. The same is true of crystal 104.

The utility of a vibration densitometer employing the structure disclosed herein is described in detail in the last mentioned patent. The embodiment of the invention illustrated in FIGS. 10, 11, 12, 13, 14 and 15 has additional utility in that erroneous readings are avoided over large density and flow rate ranges. This embodiment also has superior temperature stability over that of the prior art, and has an unusually short start up time compared to the start up times of prior art of vibration densitometers.

Cylinders 110 and 112, vane 113, and crystal 104 may be identical to those disclosed in the last mentioned patent, if desired. Tube 101 is slidable through the lower end of body 99 and is slidable through the said circular hole through cylinder 110, as is known from the said last mentioned patent.

A more detailed explanation of the operation of a vibration densitometer employing the structure disclosed herein is set forth in the said last mentioned patent.

It is common to use a preamplifier in the probe. Such a preamplifier may be employed at 114 in FIG. 15, or at any other convenient location, as desired.

Figure 16:
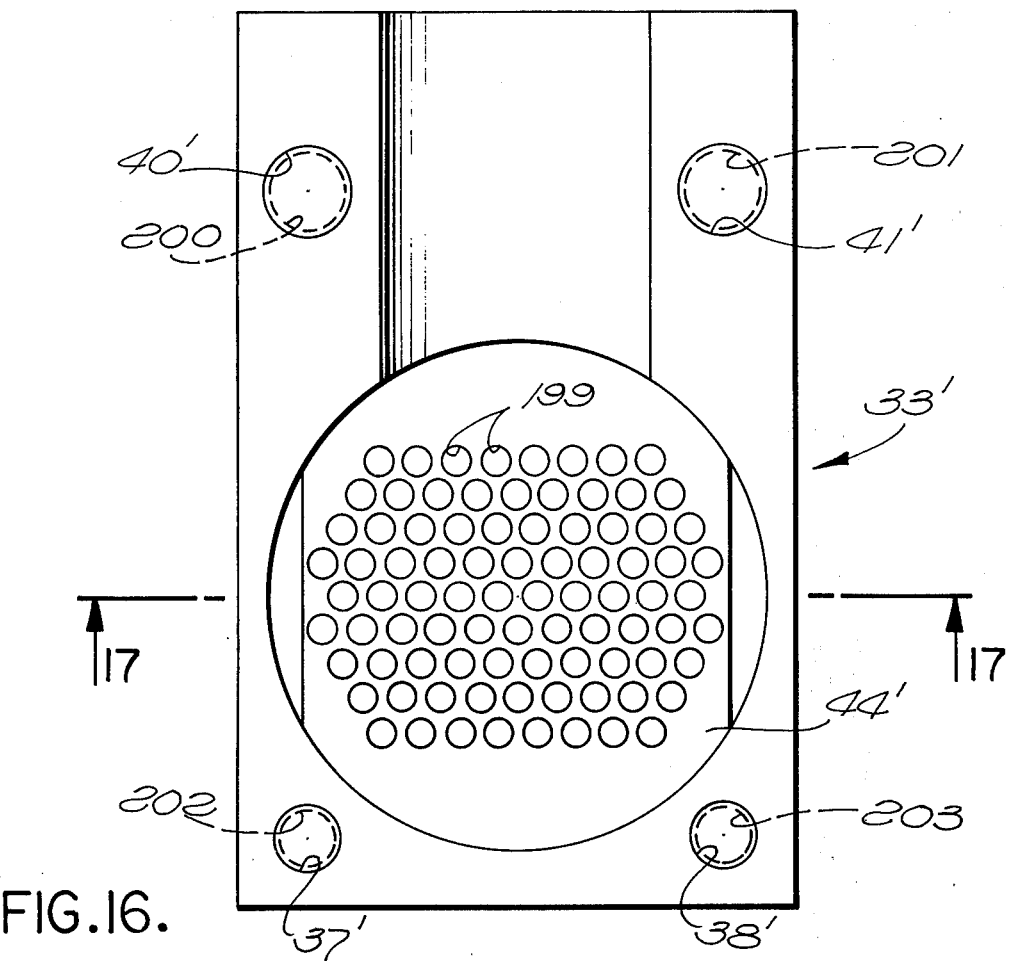
FIG. 16 is a side elevational view of one-half of an alternative probe shield.
Figure 17:
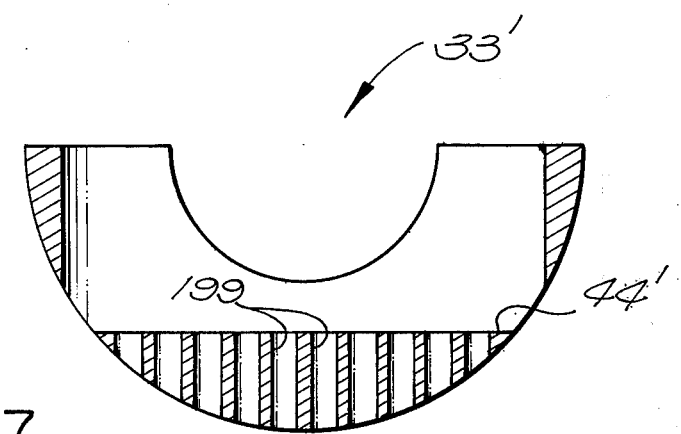
FIG. 17 is a transverse sectional view of the probe shield taken on the line 17—17 shown in FIG. 16.

FIG. 16 is a view identical to that illustrated in FIG. 6 except for the enlargement thereof and the addition of holes 199 which extend completely through the portion of a shield half 33' normal to a flat surface 44' which may, if desired, be identical to surface 44 shown in FIG. 6.

Shield half 33' is a half of a shield of an alternative construction of the present invention.

If desired, shield half 33' may have holes 40', 41', 37' and 38' identical to holes 40, 41, 37 and 38, respectively, shown in FIG. 6.

The half of the shield to mate with shield half 33' would, in elevation, look identical to shield half 33' except for the same differences illustrated in FIG. 5. For example, a section taken on the line C—C in FIG. 5 would look the same as shield half 33' in FIG. 14 except that holes similar to holes 199 would be provided and that holes 40', 41', 37' and 38' would be omitted, and holes at 200, 201, 202 and 203 would be provided. Thus, holes 199 or similar holes would be provided in both shield halves, of which shield half 33' would be a portion.

Note holes 199 in FIG. 15.

All the dimensions given herein are typical, but are not substantially critical. The diameters of holes 199 are preferably kept within the limits as set forth hereinafter.

Typically, holes 199 are located symmetrically about a vertical line through the center of shield half 33'. Typically, the distance between the center of one hole 199 and any hole adjacent thereto is 0.125 inch.

Preferably, the diameter of all the holes 199 is the same. Preferably, all of the holes 199 have a diameter of less than 0.0625 inch and greater than 0.055 inch. Perhaps the most desirable value for the diameter of each of the holes 199 is about 0.059 inch.

If desired, the construction shown in FIG. 16 may be considered to be drawn to scale. The width of surface 44' in FIG. 16 may be 1.25 inches.

Figure 18:
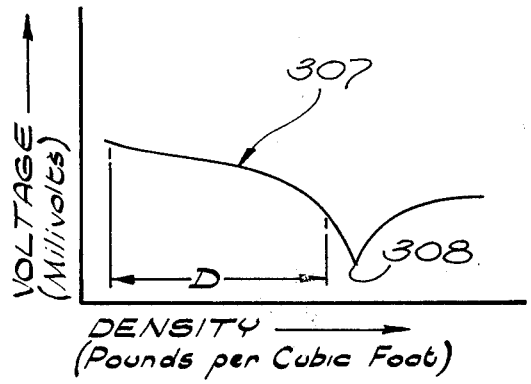
FIGS. 18, 19, 20 and 21 are graphs of a group of waveforms characteristic of the operation of the present invention.

Not infrequently, the crystal output voltage versus density curve appears as indicated at 307 in FIG. 18. Unfortunately, without the mesh 300, the curve has a notch at 308. This makes the usable span equal to D. Thus, it is an outstanding feature of the present invention that when the mesh 300 is employed, the curve 307 can be converted to the curve 307' shown in FIG. 19 without the notch 308, and the usable span thereof is increased to the extent indicated by E in FIG. 19.

Figure 19:
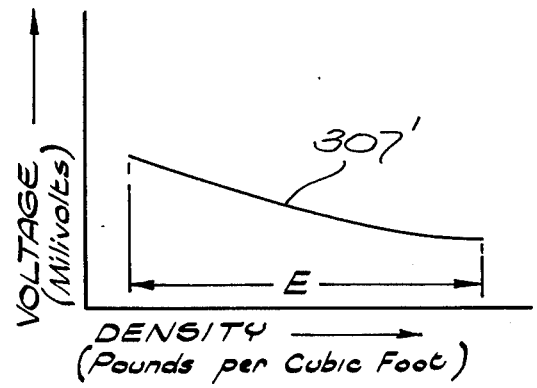
Figure 20:
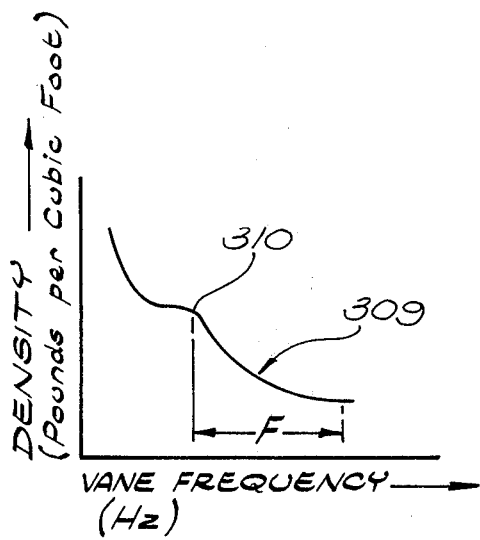
Figure 21:
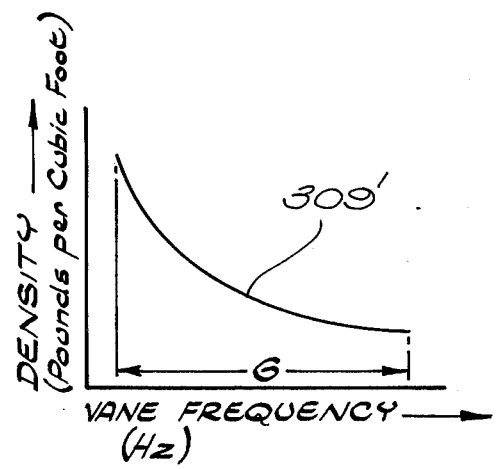

As in a fashion similar to that described in connection with FIGS. 18 and 19, in FIG. 20, the density versus vane vibration frequency curve 309 is illustrated with a discontinuity 310. Because of the discontinuity 310, the instrument has a usable range of F. Again, it is an outstanding feature of the present invention that by employing the mesh 300, the usable span F of curve 309 is increased because the curve 309 is converted to the curve 309' shown in FIG. 21 having the substantially larger usable span G.

Mesh may typically be a 50 to 100 micron rectangular Dutch twill mesh.

The word "fluid" is hereby defined to mean liquid or gas depending upon in which medium the instrument is operative.

What is claimed is:

1. In a vibration densitometer having probe means for immersion in a fluid flowing in a pipeline, apparatus for increasing the densitometer accuracy by suppressing abrupt changes in the characteristic curve of the actual density of the fluid versus the resonant frequency of vibration of the densitometer, said apparatus comprising: a hollow cylindrical well for immersion in the pipeline in a location surrounding said probe means, said well having an axis located in a position approximately normal to the direction of fluid flow in the pipeline, said well having a cover in a first plane about normal to said well axis substantially sealing the end of said well for furthest immersion in the fluid, said well having first, second and third holes through the wall thereof near the same distance from said cover, said second and third holes having axes located in respective planes through the well axis and respectively disposed about +140° and about −140° from a second plane through the axis of said first hole and through said well axis, said first hole being employed for location centrally through one half of the well from the other half thereof toward which the fluid flow is directed; and a woven mesh mounted on said well contiguous to the external surface thereof covering each of said first, second and third holes.

2. The invention as defined in claim 1, wherein said mesh is essentially cylindrical and extends completely around the external cylindrical surface of said well over a length thereof to cover all three of said first, second and third holes.

3. The invention as defined in claim 2, wherein said mesh is about a 50 to 100 micron mesh.

4. The invention as defined in claim 1, wherein said mesh is about a 50 to 100 micron mesh.

5. The invention as defined in claim 1, wherein said probe means includes a rectangular vibratable vane approximately parallel to said cover, said first, second and third holes approximately intersecting one axis of said vane, said first hole being approximately in line with said one vane axis.

6. The invention as defined in claim 1, wherein said probe means includes a rectangular vibratable vane approximately parallel to said cover, said second and third holes being located respectively above and below a third plane through the center of said vane parallel to said cover, said first hole having an axis lying in said third plane.

7. The invention as defined in claim 6, wherein said mesh is essentially cylindrical and extends completely around the external cylindrical surface of said well over a length thereof to cover all three of said first, second and third holes.

8. The invention as defined in claim 7, wherein said mesh is about a 50 to 100 micron mesh, said cover having a central hole therethrough.

9. The invention as defined in claim 6, wherein said mesh is about a 50 to 100 micron mesh.

* * * * *